United States Patent [19]
Borden et al.

[11] Patent Number: 5,266,798
[45] Date of Patent: Nov. 30, 1993

[54] HIGH SENSITIVITY, LARGE DETECTION AREA PARTICLE SENSOR FOR VACUUM APPLICATIONS

[75] Inventors: Peter Borden; Mark Nokes, both of Palo Alto; Maurits Kain, Redwood City; James Stolz, Milpitas, all of Calif.

[73] Assignee: High Yield Technology, Sunnyvale, Calif.

[21] Appl. No.: 742,798

[22] Filed: Aug. 8, 1991

Related U.S. Application Data

[62] Division of Ser. No. 582,718, Sep. 14, 1990, Pat. No. 5,132,548.

[51] Int. Cl.$^5$ .............................................. H01J 5/02
[52] U.S. Cl. ................................... 250/239; 250/573; 356/338
[58] Field of Search ............... 250/573, 574, 575, 576, 250/216, 239; 356/336, 337, 338, 339, 340, 342, 343, 244

[56] References Cited

U.S. PATENT DOCUMENTS

| | | | |
|---|---|---|---|
| 4,053,229 | 10/1977 | McCluney | 356/339 |
| 4,226,533 | 10/1980 | Snowman | 250/574 |
| 4,755,052 | 7/1988 | Giglio et al. | 356/336 |

*Primary Examiner*—David C. Nelms
*Assistant Examiner*—John R. Lee
*Attorney, Agent, or Firm*—Skjerven, Morrill, MacPherson, Franklin & Friel

[57] ABSTRACT

A particle sensor which employs the principle that a particle passing through an intense laser beam will scatter light to a photodetector which then generates a measurable signal is provided. The particle sensor uses prisms and a cylindrical lens to compress the laser beam to make it very thin along the axis of particle motion but very wide in the plane perpendicular to particle motion, thereby simultaneously providing high beam intensity for enhanced sensitivity and a large detection area. The optical components of the sensor are mounted on separate sections which allows the optical components to be separately aligned and changed so that the sensor may be easily adapted to various applications.

7 Claims, 5 Drawing Sheets

HIGH SENSITIVITY, LARGE DETECTION AREA PARTICLE SENSOR FOR VACUUM APPLICATIONS

This application is a division of application Ser. No. 07/582,718, filed Sep. 14, 1990 now U.S. Pat. No. 5,132,548.

FIELD OF THE INVENTION

This invention relates to a sensor for detecting free particle contamination over a large area of a vacuum environment.

BACKGROUND OF THE INVENTION

Particle contamination from vacuum equipment in VLSI processing is estimated to be responsible for 40% of the total yield loss. As a consequence, it is important to control particle occurrence through use of standard techniques such as statistical process control. This, in turn, requires sensitive real-time particle sensors that function reliably in the environment of the process equipment to report particle occurrence. Since statistics for particle occurrence become more reliable as more particles are counted, sensors are preferably designed to detect as many particles as possible. In addition, since the frequency of particle occurrence often increases with decreasing particle size, sensors are also preferably designed to detect as small particles as possible.

Laser based particle sensors employ the principle that a particle passing through an intense laser beam will scatter light to a photodetector which then generates a measurable signal.

U.S. Pat. No. 4,739,177 by Peter Borden describes a particle sensor in which a laser beam is repeatedly reflected back and forth between mirrors This sensor is designed to function regardless of the atmospheric pressure, and is thus appropriate for use in vacuum systems. U.S. Pat. No. 4,804,853 by Peter Borden, Laslo Szalai and Jon Munson describes a particle sensor that uses a single laser beam and photocells mounted on the sensor body parallel to the beam. This sensor will also function regardless of the local pressure and can be used in vacuum systems. Neither of these patents, however, discloses specific means for shaping the transverse cross-section of the laser beam to provide the advantages discussed below.

The sensors described in the two patents cited above use a body made from a single piece of precision machined stainless steel or aluminum. Even with the relatively few optical elements used in these sensors, such a body is expensive to manufacture because of the large number of machining operations required. In addition, making changes to the optical system to tailor the sensor to various applications is difficult and requires redesign of the body. Thus, these earlier designs suffer disadvantages in manufacturing cost and design flexibility.

SUMMARY OF THE INVENTION

A sensor according to one embodiment of this invention includes an optical system which can provide a very thin but very wide laser beam, a virtual sheet of laser light. By shaping the transverse cross-section of the beam, sensor performance can be optimized. Specifically, making a laser beam very wide in the plane perpendicular to particle motion results in a large detection area which increases the number of particles that can be detected. Making the beam very thin along the axis of particle motion results in high beam intensity, providing enhanced sensitivity, especially to smaller particles. The example of the sensor in this invention has a maximum detection area of 80 mm$^2$ and can detect particles as small as 0.2 µm in diameter. By way of example, a sensor conforming to the design described in U.S. Pat. No. 4,804,853 is able to detect particles with a minimum size of 0.3 82 m and has a detection area of about 10 mm$^2$ for particles with a diameter of 0.5 µm.

Additional features of the sensor allow tailoring of the beam profile to achieve an optimum balance between the minimum detectable particle size and the number of particles detected. Adjusting this balance is very important for optimizing sensor performance for various applications.

A sensor according to one embodiment of this invention may also include a mechanical structure in which each optical element is placed in a separate holder. The holders are slidably mounted onto steel rods, and abut against one another to form a rigid structure. This arrangement allows the optical elements in each holder to be separately aligned, and the optics configuration to be readily changed so that the sensor can be adapted for various applications. In addition, the manufacturing cost of this mechanical structure for a sensor is lower than the manufacturing cost of a single, integral sensor structure.

DETAILED DESCRIPTION OF THE INVENTION

Figure 1:
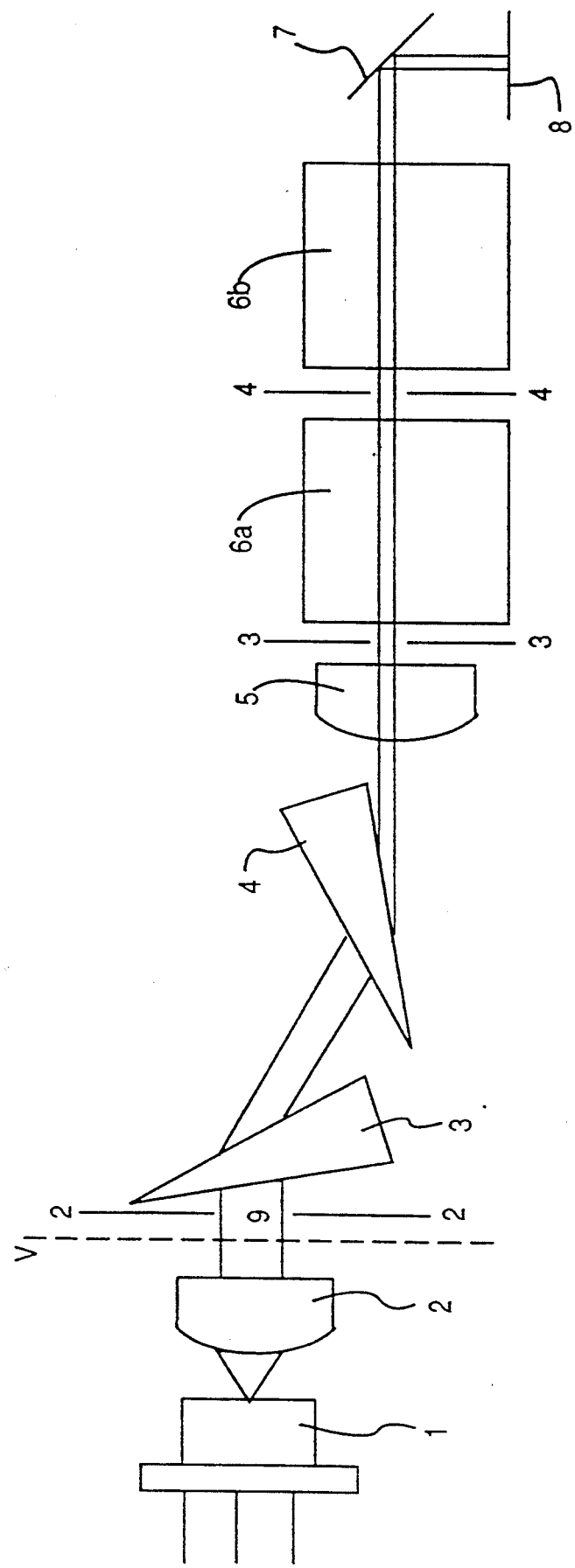
FIG. 1 is a schematic illustration of the optical components of a particle sensor according to one embodiment of this invention.
Figure 2:
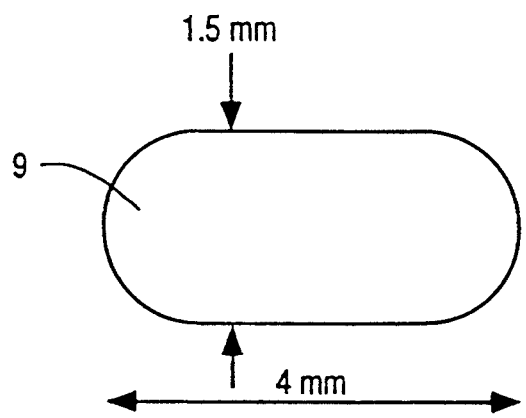
FIG. 2 illustrates the cross-sectional dimensions of a laser beam at line 2—2 of FIG. 1.

As illustrated in FIG. 1, semiconductor diode laser light source 1 emits a 30 mW laser beam 9 with a wavelength of 790 nm Diode 1 may be model 301 manufactured by Sony, for example. Beam 9 is collimated using a standard lens 2 such as Nippon Sheet Glass OPL. The cross-section of beam 9 is oval in shape, with a thickness of about 1.5 mm and a width of about 4 mm as shown in FIG. 2 taken along line 2—2 of FIG. 1. Because the cross-section is relatively large, the optical power density of beam 9 is relatively low. To increase the optical power density of beam 9, prism 3 and prism 4 are used to compress the thickness of the beam by at least a factor of 3. In the configuration shown, a factor of approximately 6 is typically achieved. The compression of beam 9 reduces the beam thickness but maintains a constant beam width. Prisms 3 and 4 can be, for example, 30-60-90 degree prisms made from SF-11 glass manufactured by Schott Glass Corp., with prism 3 set preferably at an angle of $-4.8°$ from the vertical and prism 4 set at an angle of $40.4°$ from the vertical, the vertical being indicated as the dotted line "V" in FIG. 1.

Figure 3:
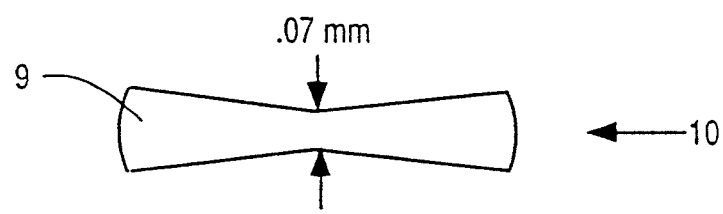
FIG. 3 illustrates the cross-sectional dimensions of a laser beam along its length between lens 5 and reflector 7 of FIG. 1.

The optical system of this invention uses optical components to create a sheet shaped beam having a width of about 4 mm and a thickness of about 0.25 mm after the beam passes through prism 4. The optical power density at this point is appropriate for detecting particles about 0.3 μm in diameter when suitable high-gain, low noise amplifier electronics are used in the sensor. However, in many cases it is necessary to detect smaller particles, as small as 0.2 μm in diameter. For this reason, cylindrical lens 5, which may be manufactured by Melles Griot, for example, is included to slightly taper the beam 9 to a focus before the beam 9 passes first photocell 6a. Cylindrical lens 5 compresses beam 9 to a thickness of less than 0.1 mm, typically 0.07 mm at focus 10, while retaining the beam width of 4 mm as illustrated in FIG. 3, a cross-section of beam 9 taken in a plane parallel to the plane of FIG. 1, between lens 5 and reflector 7. Thus, the large width of beam 9 provides a large cross-section for the detection of particles passing through the sensor, while the extremely narrow beam thickness provides a high optical power density which increases the intensity of the light scattered from particles passing through the beam.

Figure 4:
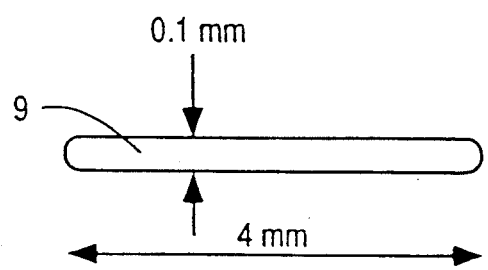
FIG. 4 illustrates the cross-sectional dimensions of a laser beam at line 4—4 of FIG. 1.

The thickness of the beam 9 at focus 10 is inversely proportional to the thickness of beam 9 as it enters cylindrical lens 5, as given by the formula $$t_{focus} = 1.22 \lambda f / t_{in}$$

where $t_{focus}$ is the thickness of beam 9 at focus 10 after passing through cylindrical lens 5, $t_{in}$ is the thickness of beam 9 entering cylindrical lens 5, $\lambda$ is the wavelength of beam 9, and f is the focal length of cylindrical lens 5. In one embodiment of this invention, $t_{in} = 0.25$ mm, $f = 19$ mm, $\lambda = 780$ nm, and $t_{focus} = 0.073$ mm. Thus, as shown in FIG. 3 the thickness of beam 9 is slightly tapered resulting in focus 10. The thickness of focus 10 can be adjusted by setting the angles of the prisms 3 and 4 to provide more or less beam compression, thereby changing $t_{in}$. The focus 10 is preferably maintained near the center of first photocell 6a to provide the best response to scattered light. Beam 9 will have its greatest optical power at the point where it is most highly compressed and focused. Therefore particles passing through beam 9 at focus 10 cause more intense scattered light and a stronger signal from photocell 6a which allows the detection of smaller particles. Beam 9 will thicken slightly and lose focus 10 as it propagates past photocells 6a and 6b. A cross-section of beam 9 shown in FIG. 4 taken along line 4—4 of FIG. 1 still has a very narrow beam about 0.1 mm thick and the same beam width of 4 mm.

It is also possible to make an extremely thin beam without a focus; however, doing so has drawbacks. The beam will diverge according to the relationship $$\theta = \lambda / \pi w_o$$

where $\theta$ is the divergence angle, $\lambda$ is wavelength of the beam, and $w_o$ is the beam thickness as it leaves a prism. For a wavelength of 800 nm and an original beam thickness of 100 microns, the divergence angle is 2.3 milliradians. For a beam length of 4 cm the beam thickness doubles along the beam length, thereby decreasing the optical power of the beam. In addition, obtaining a highly compressed, unfocused beam requires a very high compression from the prism assembly to compensate for beam divergence. Very high compression makes reproducible alignment of the beam difficult.

In one embodiment of this invention, four photocells 6a–6d such as small silicon chip photodiodes are placed adjacent to the detection area. Photocells 6a and 6b face beam 9 to detect light scattered by particles passing through beam 9 in a direction parallel to the plane of FIG. 1. Photocells 6c and 6d (not shown) will directly oppose photocells 6a and 6b.

When a particle passes through beam 9, the particle will scatter light, some of which will reach photocells 6a–6d. Photocells 6a–6d consequently generate an electrical signal which is processed by electronic circuitry substantially the same as that described in U.S. Pat. No. 4,739,177 issued Apr. 18, 1988 to Peter Borden and incorporated here by reference.

Beam 9 is terminated using reflector 7 and beam stop 8. Reflector 7 is preferably made from colored glass that is highly absorbing at the laser wavelength, such as BG39 glass manufactured by Schott Glass Corp. Reflector 7 is positioned to reflect beam 9 to beam stop 8 where the beam is nearly completely absorbed. Beam stop 8 may be a second slab of BG39 glass.

A sensor according to this invention must be protected against corrosive gasses such as reactive fluoride species used in plasma etching of silicon dioxide during semiconductor processing. A particularly vulnerable surface is the face of the photocells 6a–6d. According to one embodiment of this invention the faces of photocells 6a–6d are protected by a vacuum grease that is impervious to reactive halogens and is also transparent, such as Krytox by DuPont. The vacuum grease is applied to the interface between each photocell 6a–6d and the colored glass filters (not shown) used to cover each photocell. This grease layer is vacuum compatible and prevents gasses from encroaching into the interface of photocells 6a–6d and the colored glass filters to attack the front surface of photocells 6a–6d. The colored glass filters, made from RG9 glass manufactured by Schott Glass Corp., filter out excess ambient light.

Figure 5:
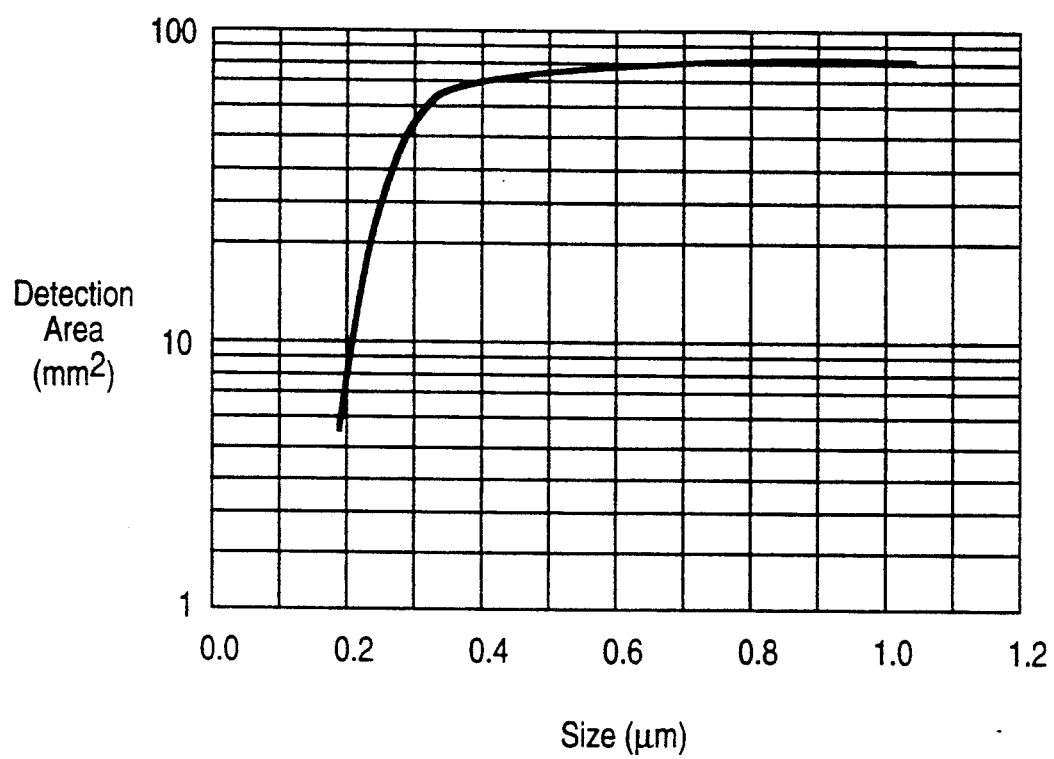
FIG. 5 is a graph of detection area vs. particle size.

The performance of a sensor according to this invention has been calculated, and has also been verified by experiment for the optical system described above in which a 30 mW laser beam is compressed by a factor of 6 using prisms 3 and 4 and further compressed and focused by cylindrical lens 5. In FIG. 5 the detection area in $mm^2$ is plotted as a function of particle size. The detection area is that area of a horizontal cross-section of beam 9 having sufficient optical power so that a particle of a certain size will scatter sufficient light to produce a signal with a 3 dB signal-to-noise ratio, meaning a detected signal with twice the amplitude of the noise level.

As particle velocity increases, the pulse of scattered light generated by the transit of the particle through beam 9 decreases in duration. Consequently, a wide bandwidth of the detection electronics associated with the photocells 6a–6d is required to detect the signal produced by the photocells when struck by light scattered from a fast moving particle. A bandwidth of 10KHz can be used to detect particles with a velocity of 0.3 m/sec but a bandwidth of 30KHz is typically used to detect particles with a velocity over 2.3 m/sec. The electronic noise level increases in proportion to the square root of the bandwidth, so a sensor able to detect faster particles due to the wider bandwidth of the detection electronics has more electronic noise and, therefore, less sensitivity. The minimum size of the detectable particles is larger for faster moving particles due to this decreased sensitivity. However, the shape of laser beam 9 counteracts this drawback by providing increased sensitivity to small particles due to the high beam intensity along the axis of particle motion and also providing a large detection area due to the large beam width. For instance, for slow particles, those moving about 0.3 m/sec, a sensor according to this invention will get usable signals from particles smaller than 0.2 $\mu$m in diameter. The maximum detection area for slow, larger particles is about 80 mm$^2$.

Figure 6:
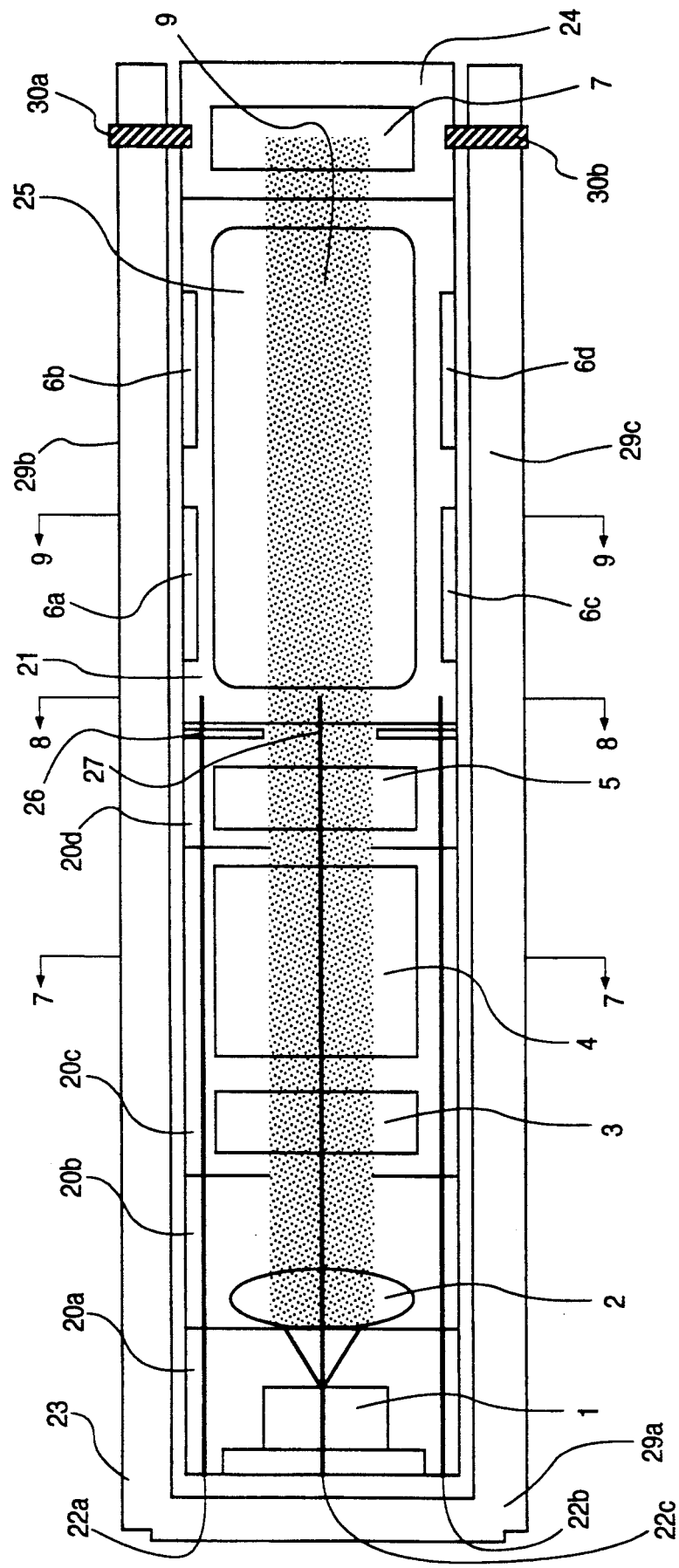
FIG. 6 shows a plan view of a particle sensor according to one embodiment of this invention.

The mechanical design of one embodiment of a sensor of this invention is illustrated in FIG. 6 which shows a plan view of the sensor. FIG. 6 shows the 4 mm width of beam 9 so that particle motion would be in a line perpendicular to the plane of the paper. Reference numbers are consistent with FIG. 1.

Each optical element, laser 1, collimating lens 2, the combination of prisms 3 and 4, and cylindrical lens 5 are mounted in a separate section 20a, 20b, 20c, and 20d, respectively, which are substantially identical. Sections 20a-20d and sensor chamber 21 are shaped as cylinders with their axes parallel to beam 9. A section cavity (not shown) in which the appropriate optical element is mounted extends through each section 20a-20d so that beam 9 can propagate through each optical element and reach sensor chamber 21. Sections 20a-20d each have three holes (not shown) through which outer rods 22a and 22b and center rod 22c slide so that each section abuts the adjacent sections. Rods 22a-22c fasten into and are supported by the sensor chamber 21. In this manner, a rigid structure is created that is insensitive to jarring or vibration.

Sensor chamber 21 includes means for mounting four photocells 6a-6d and the beam stop assembly 24, which includes reflector 7 to deflect beam 9 into the beam stop 8 (not shown). The photocells 6a-6d view the cavity 25 of sensor chamber 21 to detect light scattered by particles passing through cavity 25 and beam 9. The electrical wiring for photocells 6a-6d and laser 1 are connected to external electronics using a Kapton flexible circuit (not shown).

To ensure rigidity in order to minimize sensitivity to vibration, the sensor is partially enclosed by a cover 23 which provides an additional structural element for connecting the series of sections 20a-20d to sensor chamber 21. Cover 23 has a cylindrical portion 29a closed at one end with two extensions 29b and 29c protruding from the open end. Cylinder portion 29a fits over and completely covers all four sections 20a-20d. The two extensions 29b and 29c each extend along one side of sensor chamber 21 and are fastened to beam stop assembly 24 with screws 30a and 30b. Cavity 25 remains open for particle flow.

Figure 7:
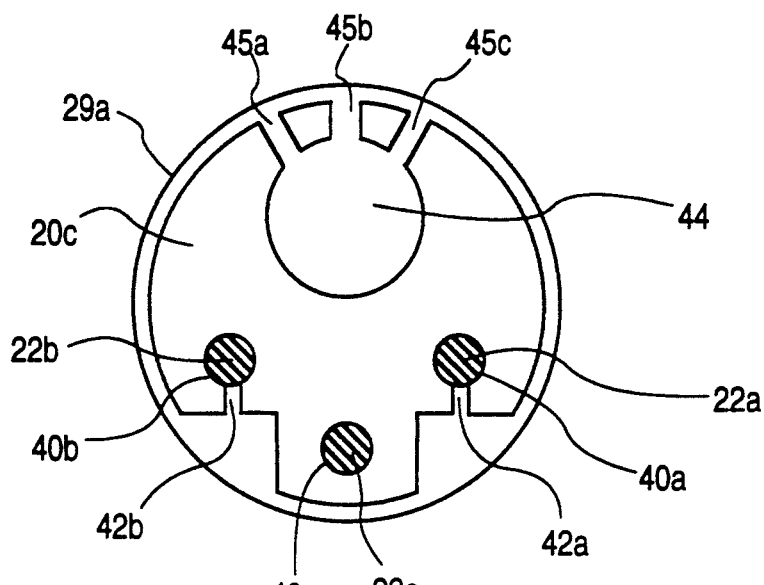
FIG. 7 is a drawing of one section used to mount an optical component according to one embodiment of this invention taken along line 7—7 of FIG. 6.

FIG. 7 is a cross-sectional view of section 20c taken along line 7—7 of FIG. 6. Section 20c is substantially shaped like a cylinder and it is tightly surrounded by cylindrical portion 29a of cover 23. Rods 22a-22c slide through holes 40a-40c, respectively to support section 20c. Set screws 42a and 42b firmly hold section 20c to the two outer rods 22a, 22b. Another pair of set screws (not shown) is positioned at the other end of section 20c also for firmly holding that section to the two outer rods 22a, 22b. Section cavity 44 extends through section 20c. Optical components such as prism 4 (not shown) are mounted in a subholder (not shown) which is inserted into section cavity 44 and fastened in place with three set screws 45a, 45b and 45c. Beam 9 will pass through section cavity 44 and any optical component positioned there.

Figure 8:
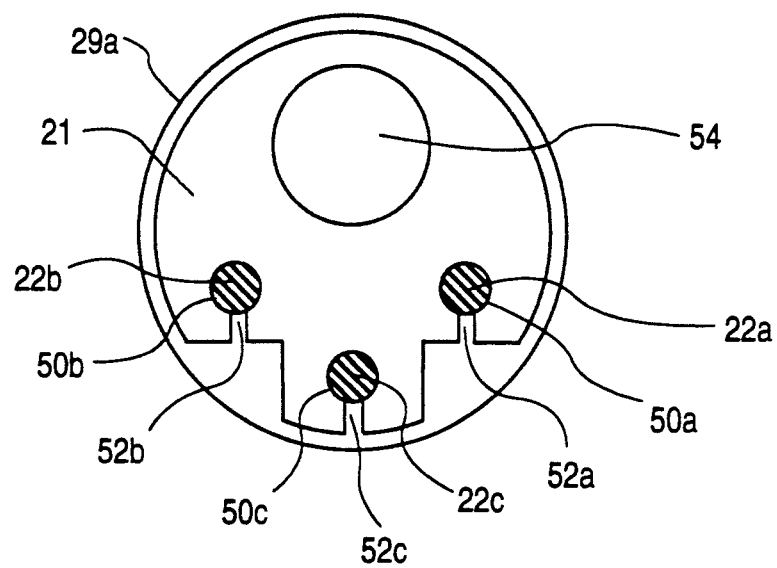
FIG. 8 is a drawing of a sensor chamber according one embodiment of this invention taken along line 8—8 of FIG. 6.

FIG. 8 is a cross-sectional view of sensor chamber 21 taken along line 8—8 of FIG. 6. Sensor chamber 21 has three holes 50a-50c which only partially extend into the sensor chamber. Rods 22a-22c are mounted in each hole 50a-50c where they are held in place by set screws 52a-52c, respectively. Opening 54 provides the entrance for laser beam 9 into sensor cavity 25. The cylindrical portion 29a of cover 23 ends at approximately this position.

Figure 9:
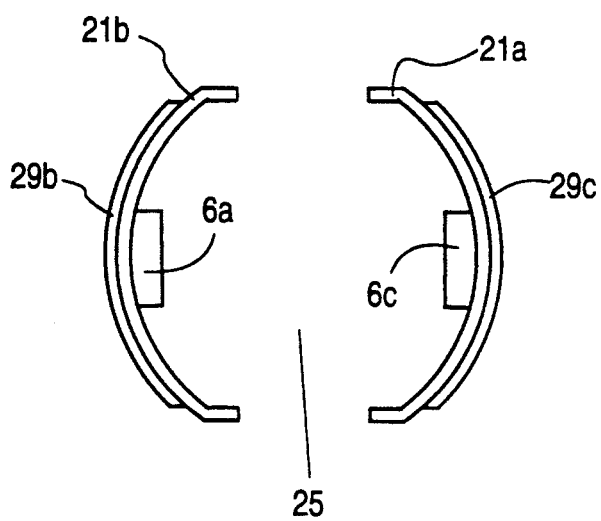
FIG. 9 is a drawing of a sensor chamber taken along line 9—9 of FIG. 6.

FIG. 9 is a cross sectional view of sensor chamber 21 taken along line 9—9 of FIG. 6. The two halves of sensor chamber 21, halves 21a and 21b, are not joined at this position so that particles falling through sensor cavity 25 will not be obstructed. Photocells 6a and 6c are mounted on the insides of halves 21a and 21b. Extensions 29b and 29c of cover 23 are positioned so as not to obstruct sensor cavity 25.

Referring again to FIG. 6, because of the high sensitivity of the sensor, it is necessary to reduce stray light to very low levels. Stray light is laser light that is not well collimated and consequently strikes the photocells. The signals caused by stray light can saturate the detection electronics. To aid in the reduction of stray light, a baffle 26 is placed after the section holding cylindrical lens 5 and prior to sensor chamber 21. Baffle 26 has a rectangular aperture 27 typically with dimensions of 1 mm by 5 mm. The 5 mm dimension is shown in FIG. 6. Baffle 26 also has three holes so that it may be mounted on rods 22a-22c similar to the mounting of sections 20a-20d.

The sensor design described above provides a number of significant advantages. Each section 20a-20d houses a single optical element, simplifying design of the entire sensor. As a result, each housed optical element can be manufactured separately and at low cost. Sections housing optical elements can be built and aligned separately. Thus, it is not necessary to simultaneously align several optical elements, thereby reducing manufacturing cost and facilitating the reproducible production of sensors Optical characteristics such as compression of the beam by the prisms or focal length of the cylindrical focusing lens can be altered by employing different sections housing different optical elements without requiring complete redesign of the sensor.

Changes may be made to the sensor described above which remain within the scope of this invention. For example, a sensor could be made without the prism assembly. Such a sensor would have a very thin beam at the focus and thus would be capable of detecting very small particles due to its high optical power. However, the beam would expand rapidly so that the area having sufficient optical power for the detection of intermediate sized particles would be reduced.

We claim:

1. A particle sensor comprising:
   means for providing a high intensity light beam, said means being housed in a first section;
   a plurality of optical elements for manipulating said light beam, said plurality of optical elements being housed in a second section, each optical element being mounted in a separate sub-section of said second section, each optical element being aligned with respect to the sub-section in which said optical element is mounted;

a sensor chamber through which said light beam propagates, said light beam in said sensor chamber being accessible to particles;

photosensor means mounted in said sensor chamber for sensing light scattered when particles pass through said light beam;

means for independently and securely attaching said first section, said second section and said sensor chamber, said first section, said second section and said sensor chamber being aligned such that said light beam passes through said optical element before entering said sensor chamber.

2. A particle sensor according to claim 1 wherein means for independently and securely attaching comprises:

a rod mounted on and extending away from said sensor chamber;

said first section defining a first opening through which said rod may slide, for mounting said first section on said rod;

said second section defining a second opening through which said rod may slide, for mounting said second section on said rod, each sub-section of said second section having an opening aligned to said second opening such that, when said second section is mounted, said rod passes through the opening of each of said sub-section;

means for fastening said first section and said second section to said rod;

said first section positioned to abut said second section.

3. A particle sensor according to claim 2 further comprising a cover which at least partly surrounds said first section, said second section and said sensor chamber to provide a second means for securely attaching said first section, said second section and said sensor chamber.

4. A particle sensor according to claim 3 further comprising a baffle having an aperture through which said light beam may pass, said baffle defining a third opening through which said rod may slide for mounting said baffle on said rod.

5. A particle sensor assembly having a plurality of optical elements, comprising:

a plurality of rods;

a plurality of substantially identical sections for housing in each section one of said optical elements, each section abutting at least one other of said sections, each section having a plurality of holes positioned such that each hole in each section is aligned with the corresponding hole in each abutting section, so as to allow one of said rods to pass therethrough, thereby fixing the positions of said sections to form a rigid structure, wherein said optical elements includes a source of high intensity light beam; and means for fastening each section to each of said rods.

6. A particle sensor assembly as in claim 5, further comprising a cover surrounding said plurality of substantially identical sections.

7. A particle sensor assembly as in claim 6, wherein said cover has a plurality of extensions for mounting light sensing means protruding beyond said sections and away from said source of high intensity light beam, each extension separated from other extensions to allow particles to pass therebetween.

* * * * *